US010159455B2

(12) United States Patent
Takanaka et al.

(10) Patent No.: US 10,159,455 B2
(45) Date of Patent: Dec. 25, 2018

(54) X-RAY DIAGNOSIS APPARATUS COMPRISING JUDGING CIRCUITRY TO JUDGE WHETHER A VOLTAGE SHOULD BE APPLIED TO A GRID OF AN X-RAY TUBE AND GRID CONTROLLING CIRCUITRY (71) Applicant: Toshiba Medical Systems Corporation, Otawara (JP)

(72) Inventors: Makoto Takanaka, Nasushiobara (JP); Kunio Shiraishi, Otawara, PA (US); Shinsuke Ooie, Yaita (JP); Kentarou Nishikawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 419 days.

(21) Appl. No.: 14/872,348

(22) Filed: Oct. 1, 2015

(65) Prior Publication Data
US 2016/0095568 A1 Apr. 7, 2016

(30) Foreign Application Priority Data

Oct. 6, 2014 (JP) ................. 2014-205883

(51) Int. Cl.
*A61B 6/00* (2006.01)
*H05G 1/08* (2006.01)
(Continued)

(52) U.S. Cl.
CPC ............. *A61B 6/487* (2013.01); *A61B 6/40* (2013.01); *A61B 6/4233* (2013.01); *A61B 6/486* (2013.01);
(Continued)

(58) Field of Classification Search
CPC ......... A61B 6/40; A61B 6/4233; A61B 6/486; A61B 6/487; A61B 6/54; A61B 6/542;
(Continued)

(56) References Cited

U.S. PATENT DOCUMENTS 4,333,011 A * 6/1982 Mester .................... H05G 1/46
378/110
4,400,823 A * 8/1983 Haendle .................. H05G 1/46
378/113
(Continued)

FOREIGN PATENT DOCUMENTS

JP 2008-073115 4/2008
JP 2011-147615 8/2011

OTHER PUBLICATIONS

Hiroshi Takano, et al., "High-speed Pulse Fluoroscopic System with High-voltage Semiconductor Switching Modules" (with English summary), Japanese Journal of Radiological Technology, vol. 57, (10), 2001, 9 pgs.
(Continued)

*Primary Examiner* — Allen C. Ho
(74) *Attorney, Agent, or Firm* — Oblon, McClelland, Maier & Neustadt, L.L.P.

(57) ABSTRACT

An X-ray diagnosis apparatus according to an embodiment includes an X-ray tube, judging circuitry, and grid controlling circuitry. The X-ray tube is configured to radiate X-rays. The judging circuitry is configured to judge whether a voltage should be applied to a grid of the X-ray tube or not, in accordance with a radiation condition. The grid controlling circuitry is configured to apply the voltage to the grid, if the judging circuitry has determined that the voltage should be applied.

8 Claims, 6 Drawing Sheets

(51) Int. Cl.
*H05G 1/30* (2006.01)
*H05G 1/32* (2006.01)
*H05G 1/34* (2006.01)
*H05G 1/42* (2006.01)
*H05G 1/44* (2006.01)
*H05G 1/58* (2006.01)
*H05G 1/60* (2006.01)
*H01J 35/04* (2006.01)

(52) U.S. Cl.
CPC ............... *A61B 6/54* (2013.01); *A61B 6/542* (2013.01); *A61B 6/56* (2013.01); *H01J 35/04* (2013.01); *H01J 35/045* (2013.01); *H05G 1/085* (2013.01); *H05G 1/30* (2013.01); *H05G 1/32* (2013.01); *H05G 1/34* (2013.01); *H05G 1/42* (2013.01); *H05G 1/44* (2013.01); *H05G 1/58* (2013.01); *H05G 1/60* (2013.01)

(58) Field of Classification Search
CPC . A61B 6/56; H05G 1/085; H05G 1/30; H05G 1/32; H05G 1/34; H05G 1/42; H05G 1/44; H05G 1/58; H05G 1/60; H01J 35/04; H01J 35/045
USPC .......................... 378/42, 62, 98.7, 137, 138
See application file for complete search history.

(56) References Cited

U.S. PATENT DOCUMENTS

| | | | | |
|---|---|---|---|---|
| 4,562,464 A * | 12/1985 | Kurihara | .................. | H04N 5/32 348/E5.086 |
| 5,572,566 A * | 11/1996 | Suzuki | .................. | A61B 6/145 378/98.2 |
| 5,617,464 A * | 4/1997 | Mika | .................. | H01J 35/04 315/169.1 |
| 5,835,554 A * | 11/1998 | Suzuki | .................. | A61B 6/145 378/98 |
| 5,949,811 A * | 9/1999 | Baba | .................. | A61B 6/4225 378/108 |
| 6,175,614 B1 * | 1/2001 | Jensen | .................. | H05G 1/36 378/95 |
| 6,215,850 B1 * | 4/2001 | Blake | .................. | H05G 1/32 378/101 |
| 6,233,309 B1 * | 5/2001 | Baptist | .................. | G03B 42/047 378/162 |
| 6,243,440 B1 * | 6/2001 | Oikawa | .................. | A61B 6/032 378/98.7 |
| 6,377,656 B1 * | 4/2002 | Ueki | .................. | A61B 6/4225 378/98.7 |
| 6,456,691 B2 * | 9/2002 | Takahashi | .................. | B82Y 10/00 378/122 |
| 6,459,765 B1 * | 10/2002 | Ganin | .................. | A61B 6/00 378/108 |
| 6,516,098 B2 * | 2/2003 | Nonaka | .................. | H01L 27/00 257/E27.001 |
| 6,553,096 B1 * | 4/2003 | Zhou | .................. | A61B 6/4028 378/122 |
| 6,570,958 B2 * | 5/2003 | Brendler | .................. | H01J 35/045 378/113 |
| 6,594,339 B1 * | 7/2003 | Alving | .................. | A61B 6/488 378/98.7 |
| 6,775,354 B1 * | 8/2004 | Roffers | .................. | H05G 1/54 378/113 |
| 6,847,698 B2 * | 1/2005 | Kaifu | .................. | A61B 6/00 250/370.07 |
| 6,944,268 B2 * | 9/2005 | Shimono | .................. | H01J 35/045 378/111 |
| 7,006,599 B2 * | 2/2006 | Okamura | .................. | A61B 6/00 250/370.08 |
| 7,010,090 B2 * | 3/2006 | Ono | .................. | A61B 6/00 378/106 |
| 7,116,752 B2 * | 10/2006 | Takahashi | .................. | A61B 6/504 378/62 |
| 7,212,610 B2 * | 5/2007 | Ishikawa | .................. | H05G 1/26 378/138 |
| 7,274,770 B2 * | 9/2007 | Nederpelt | .................. | G06T 5/40 378/97 |
| 7,280,635 B2 * | 10/2007 | Toth | .................. | A61B 6/032 378/108 |
| 7,406,154 B2 * | 7/2008 | Resnick | .................. | A61B 6/032 378/113 |
| 7,440,547 B2 * | 10/2008 | Ishiyama | .................. | A61B 6/032 378/101 |
| 7,476,027 B2 * | 1/2009 | Takenaka | .................. | G01N 23/04 378/116 |
| 7,496,180 B1 * | 2/2009 | Subraya | .................. | H01J 35/14 378/137 |
| 7,505,562 B2 * | 3/2009 | Dinca | .................. | G01N 23/201 378/57 |
| 7,529,344 B2 * | 5/2009 | Oreper | .................. | H01J 35/045 378/134 |
| 7,606,349 B2 * | 10/2009 | Oreper | .................. | G01V 5/005 378/137 |
| 7,609,815 B2 * | 10/2009 | Leung | .................. | B82Y 10/00 378/136 |
| 7,627,087 B2 * | 12/2009 | Zou | .................. | H01J 1/304 378/122 |
| 7,646,852 B2 * | 1/2010 | Harding | .................. | H05G 1/52 378/111 |
| 7,792,241 B2 * | 9/2010 | Wu | .................. | H01J 35/045 378/114 |
| 7,801,277 B2 * | 9/2010 | Zou | .................. | H01J 35/065 378/119 |
| 7,809,114 B2 * | 10/2010 | Zou | .................. | H01J 1/3048 378/122 |
| 7,826,594 B2 * | 11/2010 | Zou | .................. | H01J 1/30 378/10 |
| 8,027,433 B2 * | 9/2011 | Zou | .................. | H01J 35/06 313/447 |
| 8,358,741 B2 * | 1/2013 | Grasruck | .................. | H01J 35/045 378/113 |
| 8,396,185 B2 * | 3/2013 | Zou | .................. | A61B 6/032 378/112 |
| 8,428,329 B2 * | 4/2013 | Miyamoto | .................. | G06K 9/4647 378/42 |
| 8,447,013 B2 * | 5/2013 | Sprenger | .................. | H01J 35/04 378/122 |
| 8,487,534 B2 * | 7/2013 | Caiafa | .................. | H05G 1/32 315/111.31 |
| 8,488,742 B2 * | 7/2013 | Tsujii | .................. | A61B 6/4441 378/138 |
| 8,498,380 B2 * | 7/2013 | Behling | .................. | H01J 35/04 378/138 |
| 8,537,965 B2 * | 9/2013 | Dafni | .................. | A61B 6/032 378/4 |
| 8,675,817 B2 * | 3/2014 | Ogata | .................. | H01J 35/045 378/101 |
| 8,699,657 B2 * | 4/2014 | Baeumer | .................. | A61B 6/032 250/494.1 |
| 8,774,364 B2 * | 7/2014 | Aoki | .................. | H01J 35/045 378/104 |
| 8,971,494 B2 * | 3/2015 | Tajima | .................. | A61B 6/542 378/108 |
| 9,036,785 B2 * | 5/2015 | Saito | .................. | H01J 35/26 378/101 |
| 9,055,238 B2 * | 6/2015 | Oda | .................. | H04N 5/3765 |
| 9,055,922 B2 * | 6/2015 | Kuwabara | .................. | A61B 6/542 |
| 9,058,958 B2 * | 6/2015 | Aoki | .................. | H01J 35/04 |
| 9,060,738 B2 * | 6/2015 | Kuwabara | .................. | A61B 6/548 |
| 9,064,670 B2 * | 6/2015 | Kim | .................. | H01J 3/021 |
| 9,070,529 B2 * | 6/2015 | Tamura | .................. | H01J 35/12 |
| 9,072,154 B2 * | 6/2015 | Wang | .................. | H05G 1/10 |
| 9,076,627 B2 * | 7/2015 | Yanagisawa | .................. | H01J 35/16 |
| 9,146,326 B2 * | 9/2015 | Kuwabara | .................. | G01T 1/17 |
| 9,159,525 B2 * | 10/2015 | Yamazaki | .................. | H01J 35/06 |
| 9,281,155 B2 * | 3/2016 | Ueda | .................. | H01J 35/18 |
| 9,281,159 B2 * | 3/2016 | Tamura | .................. | H05G 1/025 |

(56) References Cited

U.S. PATENT DOCUMENTS

| | | | |
|---|---|---|---|
| 9,351,699 B2* | 5/2016 | Kuwabara | A61B 6/542 |
| 9,373,478 B2* | 6/2016 | Tamura | H01J 35/12 |
| 9,374,881 B2* | 6/2016 | Aoki | H05G 1/54 |
| 9,412,552 B2* | 8/2016 | Aoki | H01J 35/08 |
| 9,414,801 B2* | 8/2016 | Kim | B25J 9/1694 |
| 9,506,877 B2* | 11/2016 | Koh | G01N 23/046 |
| 9,508,522 B2* | 11/2016 | Park | H01J 19/44 |
| 9,514,910 B2* | 12/2016 | Yanagisawa | H01J 35/20 |
| 9,517,043 B2* | 12/2016 | Tamura | A61B 6/025 |
| 9,538,099 B2* | 1/2017 | Kim | A61B 6/4233 |
| 9,547,900 B2* | 1/2017 | Fuchigami | A61B 6/4417 |
| 9,577,766 B2* | 2/2017 | Zhao | H01J 31/49 |
| 9,633,814 B2* | 4/2017 | Oikawa | A61B 6/405 |
| 9,659,739 B2* | 5/2017 | Bathe | H01J 35/14 |
| 9,668,331 B2* | 5/2017 | Takahashi | H04N 5/32 |
| 9,675,309 B2* | 6/2017 | Kim | A61B 6/4266 |
| 9,700,268 B2* | 7/2017 | Kang | A61B 6/542 |
| 9,724,061 B2* | 8/2017 | Hyung | A61B 6/469 |
| 9,747,703 B2* | 8/2017 | Yi | G06T 11/006 |
| 9,750,477 B2* | 9/2017 | Kitagawa | A61B 6/542 |
| 9,761,404 B2* | 9/2017 | Tang | H01J 35/06 |
| 9,775,225 B2* | 9/2017 | Tamura | A61B 6/032 |
| 9,788,809 B2* | 10/2017 | Hiroike | A61B 6/54 |
| 9,848,845 B2* | 12/2017 | Tajima | A61B 6/542 |
| 9,888,901 B2* | 2/2018 | Iwai | A61B 6/542 |
| 9,895,123 B2* | 2/2018 | Kim | A61B 6/5205 |
| 9,931,090 B2* | 4/2018 | Sakaguchi | A61B 6/463 |
| 9,980,690 B2* | 5/2018 | Muroi | A61B 6/463 |
| 10,022,102 B2* | 7/2018 | Okada | A61B 6/542 |

OTHER PUBLICATIONS

Office Action dated Jul. 24, 2018 in Japanese Application No. 2014-205883.

* cited by examiner

X-RAY DIAGNOSIS APPARATUS COMPRISING JUDGING CIRCUITRY TO JUDGE WHETHER A VOLTAGE SHOULD BE APPLIED TO A GRID OF AN X-RAY TUBE AND GRID CONTROLLING CIRCUITRY

CROSS-REFERENCE TO RELATED APPLICATIONS

This application is based upon and claims the benefit of priority from Japanese Patent Application No. 2014-205883, filed on Oct. 6, 2014; the entire contents of which are incorporated herein by reference.

FIELD

Embodiments described herein relate generally to an X-ray diagnosis apparatus.

BACKGROUND

Conventionally, while using an X-ray diagnosis apparatus, when an X-ray pulse is radiated onto an examined subject (hereinafter, "patient") P, it may be observed that the descending waveform of the pulse has a gradual descent. Such a gradually-descending waveform (hereinafter, "wave tail") not only makes no contribution to the imaging process, but also causes unnecessary radiation exposure for the patient P. It is known that the lower the output level of an X-ray pulse is, the more easily a wave tail occurs. For this reason, during a fluoroscopy process, which has a lower output level than an image taking process, a technique called grid control is used by which wave tails are eliminated (cut off) by applying a voltage to a grid of the X-ray tube and inhibiting thermal electrons from being released.

DETAILED DESCRIPTION

An X-ray diagnosis apparatus according to an embodiment includes an X-ray tube, judging circuitry, and grid controlling circuitry. The X-ray tube is configured to radiate X-rays. The judging circuitry is configured to judge whether a voltage should be applied to a grid of the X-ray tube or not, in accordance with a radiation condition. The grid controlling circuitry is configured to apply the voltage to the grid, if the judging circuitry has determined that the voltage should be applied.

Exemplary embodiments of an X-ray diagnosis apparatus will be explained, with reference to the accompanying drawings.

First Embodiment

Figure 1:
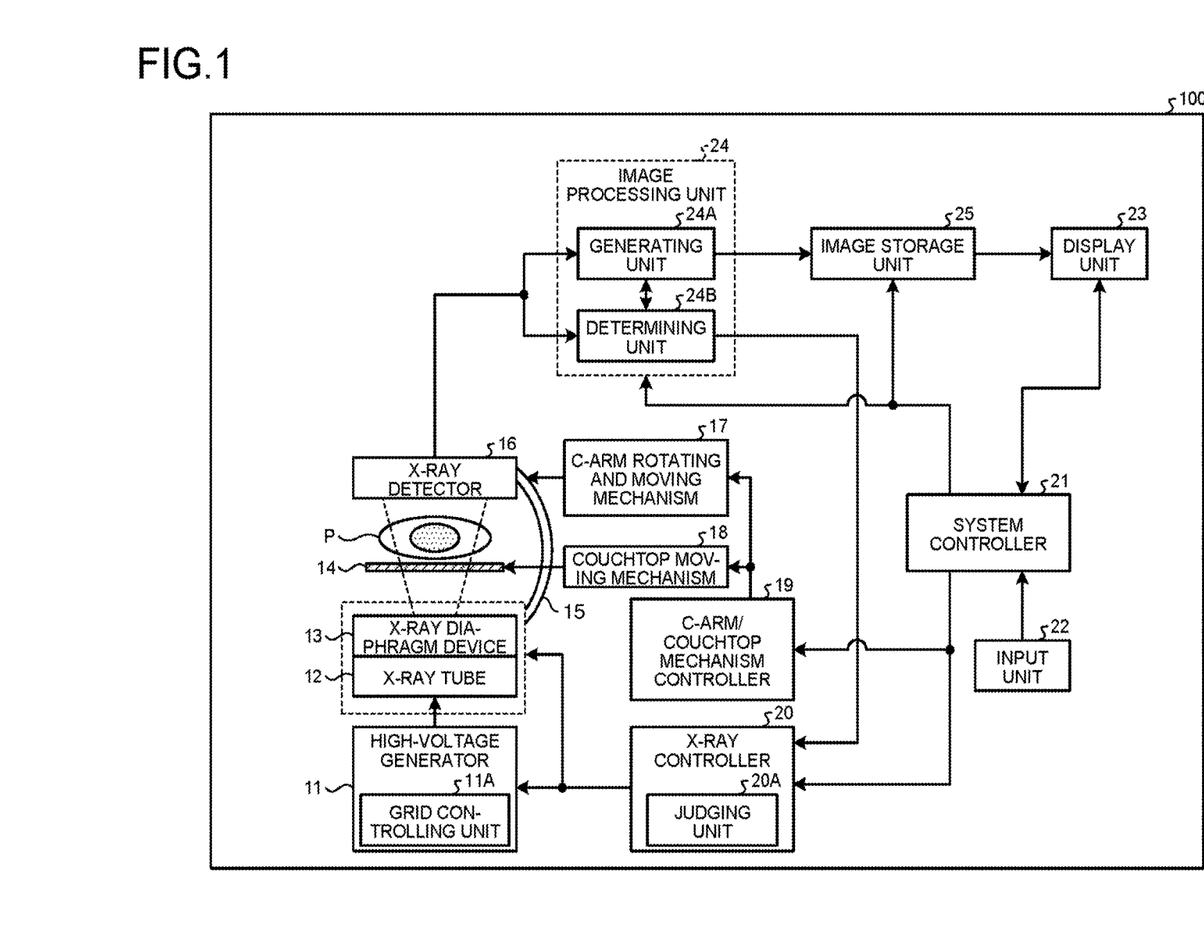
FIG. 1 is a diagram of an exemplary configuration of an X-ray diagnosis apparatus according to a first embodiment.

FIG. 1 is a diagram of an exemplary configuration of an X-ray diagnosis apparatus 100 according to a first embodiment. As illustrated in FIG. 1, the X-ray diagnosis apparatus 100 according to the first embodiment includes a high-voltage generator 11, an X-ray tube 12, an X-ray diaphragm device 13, a couchtop 14, a C-arm 15, and an X-ray detector 16. Further, the X-ray diagnosis apparatus 100 according to the first embodiment also includes a C-arm rotating and moving mechanism 17, a couchtop moving mechanism 18, a C-arm/couchtop mechanism controller 19, an X-ray controller 20, a system controller 21, an input unit 22, and a display unit 23. Further, the X-ray diagnosis apparatus 100 according to the first embodiment also includes an image processing unit 24 and an image storage unit 25.

Further, as illustrated in FIG. 1, the high-voltage generator 11 includes a grid controlling unit 11A. The X-ray controller 20 includes a judging unit 20A. Further, the image processing unit 24 includes a generating unit 24A and a determining unit 24B. The patient P is not included in the X-ray diagnosis apparatus 100.

The high-voltage generator 11 is configured, under control of the X-ray controller 20, to generate a high voltage and to supply the generated high voltage to the X-ray tube 12. The X-ray tube 12 is configured to generate X-rays by using the high voltage supplied from the high-voltage generator 11. In other words, the high-voltage generator 11 adjusts the dose of X-rays generated from the X-ray tube 12, by adjusting an X-ray tube voltage and an X-ray tube current supplied to the X-ray tube 12. Processes performed by the grid controlling unit 11A included in the high-voltage generator 11 will be explained later.

The X-ray diaphragm device 13 is configured, under control of the X-ray controller 20, to limit the X-rays generated by the X-ray tube 12 so that the X-rays are selectively radiated onto a region of interest of the patient P. For example, the X-ray diaphragm device 13 includes four slidable limiting vanes. Under the control of the X-ray controller 20, the X-ray diaphragm device 13 limits the X-rays generated by the X-ray tube 12 by sliding the limiting vanes and causes the limited X-rays to be radiated onto the patient P. The couchtop 14 is a bed on which the patient P is placed and is disposed on a couch (not illustrated).

The C-arm 15 is configured to hold the X-ray tube 12, the X-ray diaphragm device 13, and the X-ray detector 16. The C-arm 15 arranges the X-ray tube 12 and the X-ray diaphragm device 13 to oppose the X-ray detector 16, while the patient P is interposed therebetween.

The X-ray detector 16 is configured to detect X-rays that have passed through the patient P. For example, the X-ray detector 16 includes detecting elements arranged in a matrix formation. The detecting elements convert the X-rays that have passed through the patient P into electrical signals and store the electrical signals therein. The X-ray detector 16 transmits the electrical signals stored in the detecting elements to the image processing unit 24 as detection data.

The C-arm rotating and moving mechanism 17 is a mechanism configured to rotate and move the C-arm 15. The couchtop moving mechanism 18 is a mechanism configured to move the couchtop 14. The C-arm/couchtop mechanism controller 19 is configured to, under control of the system controller 21, adjust the rotation and the moving of the C-arm 15 and the moving of the couchtop 14, by controlling the C-arm rotating and moving mechanism 17 and the couchtop moving mechanism 18.

The X-ray controller 20 is configured to cause the X-rays to be radiated onto the patient P, by controlling the high-voltage generator 11, the X-ray tube 12, and the X-ray diaphragm device 13. For example, under control of the system controller 21, the X-ray controller 20 controls the dose of X-rays radiated onto the patient P and turns on and off of the X-rays, by controlling the high-voltage generator 11 so as to adjust the X-ray tube voltage and the X-ray tube current supplied to the X-ray tube 12. Further, for example, under the control of the system controller 21, the X-ray controller 20 controls the radiation range of the X-rays radiated onto the patient P, by adjusting the aperture of the limiting vanes included in the X-ray diaphragm device 13. Processes performed by the judging unit 20A included in the X-ray controller 20 will be explained later.

The image processing unit 24 is configured to perform processes related to images. For example, the generating unit 24A is configured to generate X-ray image data by using the detection data detected by the X-ray detector 16. More specifically, the generating unit 24A generates the X-ray image data by performing a current/voltage conversion process, an Analog/Digital (A/D) conversion process, a parallel/serial conversion process, and/or the like, on the electrical signals received from the X-ray detector 16. Further, the generating unit 24A stores the generated image data into the image storage unit 25. The image storage unit 25 is configured to store therein the image data generated by the image processing unit 24. Processes performed by the determining unit 24B included in the image processing unit 24 will be explained later.

The input unit 22 is configured to receive various types of instructions from an operator (e.g., a medical doctor, a medical technician, or the like) who operates the X-ray diagnosis apparatus 100. For example, the input unit 22 includes a mouse, a keyboard, a button, a trackball, a joystick, and/or the like. The input unit 22 transfers the instructions received from the operator to the system controller 21.

The display unit 23 is configured to display a Graphical User Interface (GUI) used for receiving instructions from the operator and any of the image data stored in the image storage unit 25. For example, the display unit 23 includes a monitor. The display unit 23 may include two or more monitors.

The system controller 21 is configured to control overall operations of the X-ray diagnosis apparatus 100. For example, the system controller 21 causes the X-rays to be radiated onto the patient P, by controlling the X-ray controller 20 according to an instruction from the operator transferred thereto from the input unit 22. Further, for example, the system controller 21 adjusts the rotation and the moving of the C-arm 15 and the moving of the couchtop 14, by controlling the C-arm/couchtop mechanism controller 19 according to an instruction from the operator.

Further, the system controller 21 controls image processing processes and analyzing processes performed by the image processing unit 24, according to instructions from the operator. Further, the system controller 21 exercises controls so that the GUI used for receiving instructions from the operator as well as any of the images stored in the image storage unit 25 are displayed on the monitor included in the display unit 23.

During an X-ray image diagnosing process, when an X-ray pulse is radiated onto the patient P, it may be observed that the descending waveform of the pulse has a gradual descent. Such a gradually-descending waveform (hereinafter, "wave tail") not only makes no contribution to the imaging process, but also causes unnecessary radiation exposure for the patient P.

Figure 2A:
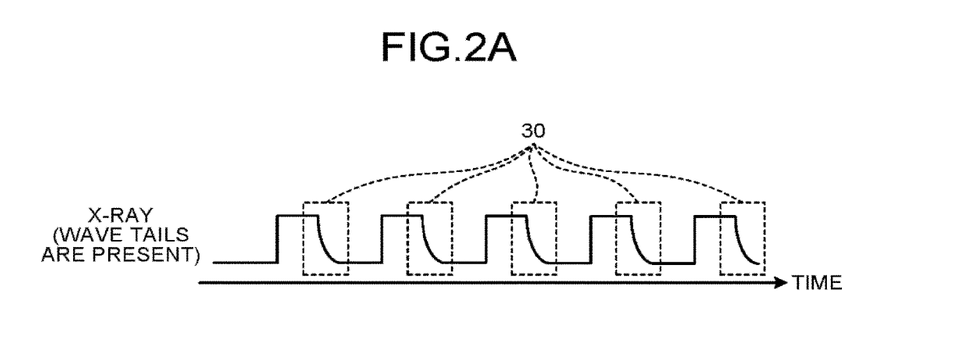
FIG. 2A is a drawing for explaining wave tails.
Figure 2B:
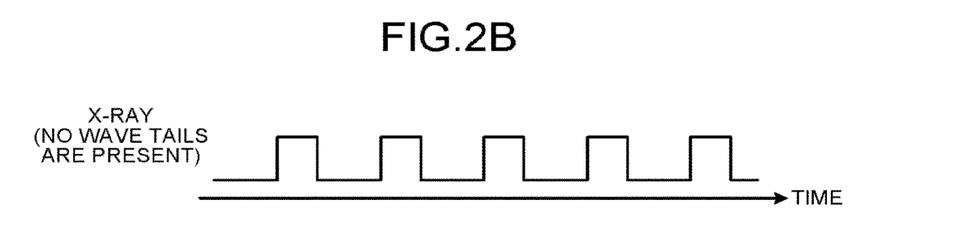
FIG. 2B is another drawing for explaining the wave tails.

FIGS. 2A and 2B are drawings for explaining the wave tails. FIG. 2A illustrates an example of a pulse waveform of X-rays having wave tails 30. FIG. 2B illustrates an example of a pulse waveform of X-rays having no wave tails. In FIGS. 2A and 2B, the horizontal direction corresponds to time (elapsed time). FIGS. 2A and 2B illustrate the examples in which a plurality of pulses are radiated in series, for example, during a pulse fluoroscopy process, a continuous image taking process, or the like. However, situations in which wave tails occur are not limited to these examples. The wave tails represent a phenomenon that can similarly occur when a pulse is radiated only once during a continuous fluoroscopy process, a single image taking process, or the like.

As illustrated in FIG. 2A, when a waveform has the wave tails 30, the descending waveforms of the pulses each have a gradual descent. The lower the level of the X-ray tube current of the X-ray tube 12 is, the more easily the wave tails 30 occur. Because what is used in the imaging process is X-rays having rectangular waveforms (see FIG. 2B), the wave tails 30 not only make no contribution to the imaging process, but also cause unnecessary radiation exposure for the patient P.

The technique called grid control is used for eliminating (cutting off) the wave tails 30. The grid control is a technique by which the wave tails 30 are eliminated by applying a voltage to a grid of the X-ray tube 12 and inhibiting thermal electrons from being released.

Figure 3:
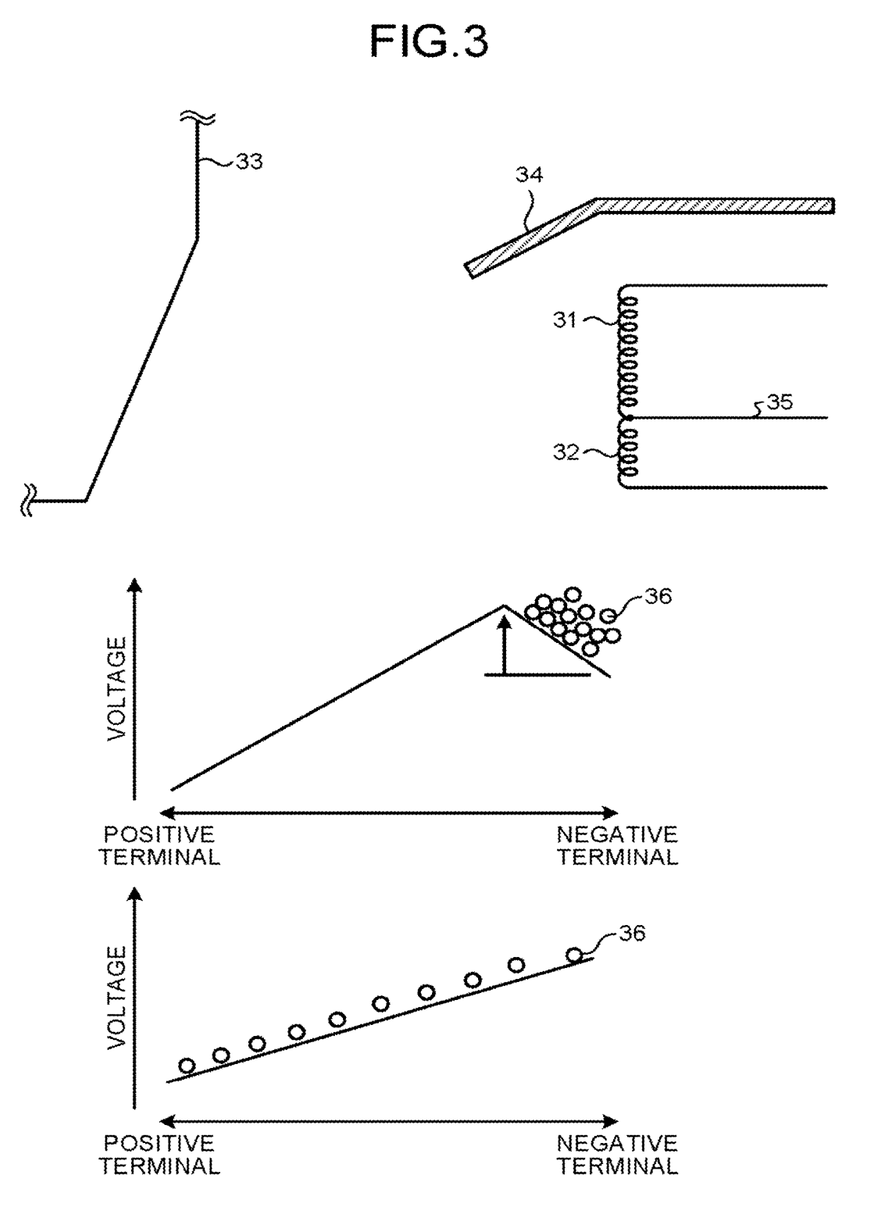
FIG. 3 is a drawing for explaining grid control.

FIG. 3 is a drawing for explaining the grid control. FIG. 3 illustrates a relationship between an internal structure of the X-ray tube 12 and releasing of thermal electrons. The top section of FIG. 3 illustrates an example of the internal structure of the X-ray tube 12 that includes a large-focus filament 31, a small-focus filament 32, a target 33, a grid 34, and the like. Further, in the middle section of FIG. 3 is a chart indicating a relationship between the voltage in a position between the positive terminal and the negative terminal and movements of thermal electrons 36, while the grid control is turned on. Further, in the bottom section of FIG. 3 is a chart indicating a relationship between the voltage in a position between the positive terminal and the negative terminal and movements of thermal electrons 36, while the grid control is turned off. The positional relationships between the positive terminal and the negative terminal correspond to one another among the top section, the middle section, and the bottom section of FIG. 3.

As illustrated in the top section and the bottom section of FIG. 3, while the grid control is turned off, the thermal electrons 36 are released from the large-focus filament 31 and the small-focus filament 32 serving as the negative terminal. As a result of the thermal electrons 36 colliding with the target 33 serving as the positive terminal, X-rays are generated. In this situation, when the grid control is turned on, a voltage (which may be referred to as a grid voltage or a bias voltage) is applied to a position between a common element 35 provided between the large-focus filament 31 and the small-focus filament 32 and the grid 34. Accordingly, as illustrated in the middle section of FIG. 3, as a result of inhibiting the thermal electrons 36 from being released, the generation of X-rays is inhibited. For example, by turning on the grid control at the time when each of the X-ray pulses descends, it is possible to inhibit the occurrence of the wave tails 30 and to arrange each of the X-ray pulses to have a rectangular waveform (see FIG. 2B).

When the grid control is exercised as described above, for example, if the radiation conditions under which the X-rays are radiated involve a high voltage or a high electric current like during an image taking process, there may be some situations where the requirement deviates from the specifications of the X-ray tube 12. Further, generally speaking, X-ray radiation conditions for a fluoroscopy process involve a lower voltage and a lower electric current than X-ray radiation conditions for an image taking process, and wave tails 30 are therefore more likely to occur. Accordingly, the grid control is widely used for pulse fluoroscopy processes.

Incidentally, due to the development in the image processing technology in recent years, it is possible to obtain images having high image quality even by using a small dose of X-rays. In addition, the demand for decreasing radiation exposure of patients P is becoming higher. With these situations in the background, it is desirable to keep X-ray radiation conditions low, not only for fluoroscopy processes, but also for image taking processes. However, if the radiation conditions are low, wave tails may occur even during image taking processes, and unnecessary radiation exposure for the patient P may increase.

To cope with these situations, the X-ray diagnosis apparatus 100 according to the first embodiment makes it possible to appropriately reduce unnecessary radiation exposure caused by the wave tails 30, by performing following the processes.

In the first embodiment, an example will be explained below in which, when a fluoroscopy process is first performed on a certain patient P followed by an image taking process, unnecessary radiation exposure caused by the wave tails 30 is appropriately reduced during the image taking process. However, the possible embodiments are not limited to this example. Other embodiments will be explained in a second embodiment and thereafter.

In the description of the embodiments hereinafter, a technical method used for either directly or indirectly recording information included in an X-ray pattern on an image receiving plane will be referred to as an "image taking process". Further, among different types of image taking processes, a process of recording an X-ray pattern formed with a series of either regular or irregular loads will be referred to as a "continuous image taking process". Further, a technical method used for arranging a series of X-ray patterns into visible images either continuously or cyclically and having the visible images continuously displayed will be referred to as a "fluoroscopy process". Among different types of fluoroscopy processes, a process of continuously radiating X-rays over the entire time period of a fluoroscopy process will be referred to as a "continuous fluoroscopy process", whereas a process of intermittently radiating pulse-form X-rays will be referred to as a "pulse fluoroscopy process". The present embodiment is able to achieve an advantageous effect, regardless of the definitions of the image taking processes and the fluoroscopy processes. In other words, the present embodiment makes it possible to appropriately reduce unnecessary radiation exposure caused by the wave tails, regardless of whether the X-ray pattern is recorded or not, whether the X-ray pattern is displayed or not, and the mode in which the X-ray pattern is displayed.

Returning to the description of FIG. 1, the determining unit 24B is configured to determine radiation conditions, on the basis of the X-ray detection data detected by the X-ray detector 16. For example, the determining unit 24B determines radiation conditions for an image taking process performed on the patient P, on the basis of the X-ray detection data detected by the X-ray detector 16 during a fluoroscopy process performed on the patient P.

In one example, the determining unit 24B determines the X-ray radiation conditions by performing an Automatic Brightness Control (ABC) process. In this situation, the ABC process is a process of automatically adjusting brightness levels of pieces of image data to be at a certain level by varying the radiation conditions of each of the pulses, when the plurality of pieces of image data are obtained by using the plurality of pulses. For example, the determining unit 24B obtains a piece of image data generated by the generating unit 24A with respect to a pulse. Subsequently, the determining unit 24B calculates an average brightness value on the inside of a region of interest that was set in advance by the operator within the obtained piece of image data. After that, the determining unit 24B compares the calculated average brightness value with a reference value that was set in advance. In this situation, if the average brightness value is larger than the reference value, the determining unit 24B determines the X-ray tube voltage [kV] and the X-ray tube current [mA] to have lower values as X-ray radiation conditions, so as to make the average brightness value of the subsequently-generated image smaller. On the contrary, if the average brightness value is smaller than the reference value, the determining unit 24B determines the radiation conditions to have larger values, so as to make the average brightness value of the subsequently-generated image larger. After that, the determining unit 24B outputs the determined radiation conditions to the judging unit 20A included in the X-ray controller 20.

As explained above, the determining unit 24B automatically adjusts the brightness levels of the pieces of image data to be at the certain level, by exercising feedback control while using the already-generated image data. In this situation, the ABC process described above is applicable not only to situations where a plurality of pieces of image data are obtained by using a plurality of pulses, for example, during a continuous image taking process or a pulse fluoroscopy process, but also to situations where, as explained in the present embodiment, radiation conditions are determined for an image taking process (a single image taking process) that is performed after a fluoroscopy process.

In the explanation above, the example is explained in which the X-ray tube voltage [kV] and the X-ray tube current [mA] of the X-ray tube 12 are adjusted as the radiation conditions; however, possible embodiments are not limited to this example. For instance, it is also acceptable to adjust only one selected from between the X-ray tube voltage [kV] and the X-ray tube current [mA]. Alternatively, for example, the determining unit 24B may determine an X-ray tube voltage [kV] and an X-ray tube current time product [mAs].

Further, for example, it is also acceptable to present the radiation conditions determined by the determining unit 24B to the operator, so that the operator makes a final decision on the radiation conditions. In other words, the determining unit 24B presents the determined radiation conditions to the operator and receives either a confirmation or a change from the operator. After that, when the operator has made the confirmation or a change on the radiation conditions and has subsequently performed an operation to determine the radiation conditions, the determining unit 24B outputs the radiation conditions determined by the operator to the judging unit 20A included in the X-ray controller 20. In other words, the determining unit 24B functions as a setting unit configured to set the radiation conditions.

The X-ray controller 20 is configured to cause the X-rays to be radiated onto the patient P, by controlling the high-voltage generator 11, the X-ray tube 12, and the X-ray diaphragm device 13, for example, on the basis of the radiation conditions determined by the determining unit 24B. Further, in the X-ray controller 20, the judging unit 20A performs processes described below.

The judging unit 20A is configured to judge whether a voltage should be applied to the grid 34 of the X-ray tube 12 or not, in accordance with the radiation conditions of the X-rays radiated from the X-ray tube 12. For example, when X-rays are radiated on the basis of radiation conditions after the radiation conditions are determined by the determining unit 24B, the judging unit 20A judges whether a voltage should be applied to the grid 34 or not, in accordance with the determined radiation conditions.

In one example, if the X-ray tube voltage [kV] and the X-ray tube current [mA] of the X-rays determined as the radiation conditions are both lower than respective threshold values that are set in advance, the judging unit 20A determines that a voltage should be applied to the grid 34. For example, the judging unit 20A judges whether the X-ray tube voltage [kV] determined by the determining unit 24B is equal to or lower than a first threshold value. If the X-ray tube voltage [kV] is equal to or lower than the first threshold value, the judging unit 20A further judges whether the X-ray tube current [mA] determined by the determining unit 24B is equal to or lower than a second threshold value. If the X-ray tube current [mA] is equal to or lower than the second threshold value, the judging unit 20A determines that the grid control should be exercised for the determined radiation conditions. After that, the judging unit 20A notifies the grid controlling unit 11A included in the high-voltage generator 11 of the judgment result indicating that the grid control should be exercised.

On the contrary, if the X-ray tube voltage [kV] is higher than the first threshold value or if the X-ray tube current [mA] is higher than the second threshold value, the judging unit 20A determines that the grid control shall not be exercised for the determined radiation conditions. After that, the judging unit 20A notifies the grid controlling unit 11A included in the high-voltage generator 11 of the judgment result indicating that the grid control shall not be exercised.

As explained above, the judging unit 20A judges whether a voltage should be applied to the grid of the X-ray tube 12 or not, in accordance with the radiation conditions determined by the determining unit 24B. In the present example, the first threshold value and the second threshold value are determined on the basis of the specifications of the X-ray tube 12. In other words, the threshold values are set so as to appropriately inhibit the occurrence of wave tails within such a range where the radiation conditions satisfy the specifications of the X-ray tube 12.

The grid controlling unit 11A is configured to apply a voltage to the grid 34, if the judging unit 20A has determined that the voltage should be applied. For example, if the judging unit 20A has determined that a voltage should be applied, the grid controlling unit 11A inhibits the occurrence of wave tails, by exercising the grid control illustrated in FIG. 3.

For example, if the judgment result received from the judging unit 20A indicates that the grid control should be exercised, the grid controlling unit 11A applies a voltage to the grid 34, at the time when the pulse descends after the X-ray pulse is radiated on the basis of the corresponding radiation conditions. With this configuration, the grid controlling unit 11A inhibits the occurrence of wave tails caused by the radiation of the pulse.

On the contrary, if the judgment result received from the judging unit 20A indicates that the grid control shall not be exercised, the grid controlling unit 11A does not apply a voltage to the grid 34, even if an X-ray pulse is radiated on the basis of the corresponding radiation conditions.

As explained above, the grid controlling unit 11A exercises the grid control when, for example, the judging unit 20A has determined that a voltage should be applied.

Figure 4:
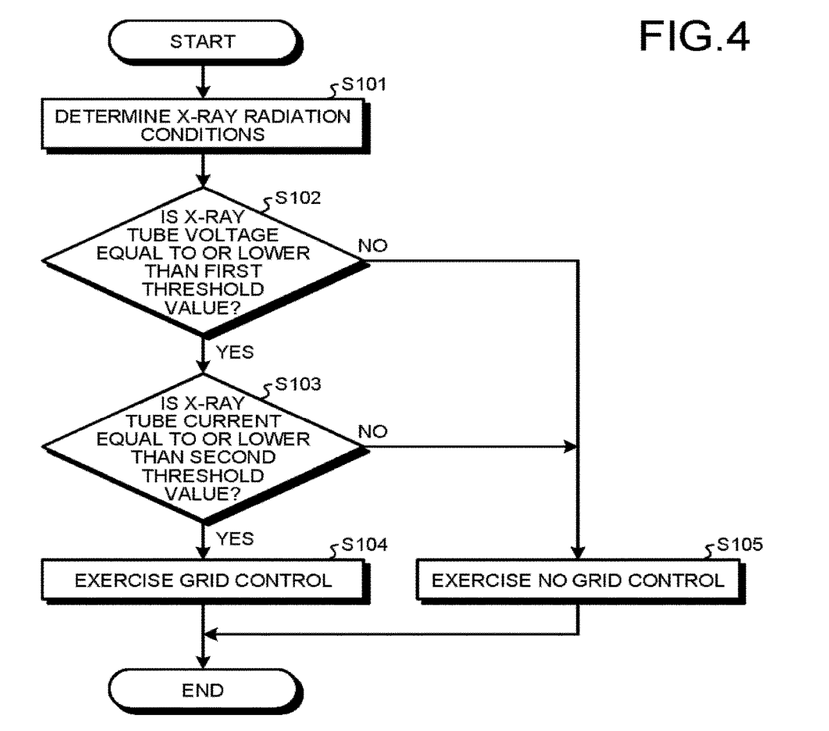
FIG. 4 is a flowchart for explaining a process performed by the X-ray diagnosis apparatus according to the first embodiment.

FIG. 4 is a flowchart for explaining a process performed by the X-ray diagnosis apparatus 100 according to the first embodiment. In the example illustrated in FIG. 4, a setting is established in advance that radiation conditions for an image taking process are determined on the basis of X-ray radiation conditions for a fluoroscopy process. The processes illustrated in FIG. 4 are performed after the fluoroscopy process has been performed.

As illustrated in FIG. 4, when the fluoroscopy process has been performed, the determining unit 24B determines X-ray radiation conditions on the basis of X-ray detection data detected by the X-ray detector 16 (step S101). For example, the determining unit 24B determines the X-ray radiation conditions by performing an Automatic Brightness Control (ABC) process.

Subsequently, the judging unit 20A judges whether the X-ray tube voltage [kV] determined by the determining unit 24B is equal to or lower than the first threshold value (step S102). If the X-ray tube voltage [kV] is equal to or lower than the first threshold value (step S102: Yes), the judging unit 20A further judges whether the X-ray tube current [mA] determined by the determining unit 24B is equal to or lower than the second threshold value (step S103). If the X-ray tube current [mA] is equal to or lower than the second threshold value (step S103: Yes), the judging unit 20A determines that the grid control should be turned on, i.e., the grid control should be exercised for the determined radiation conditions (step S104). After that, the judging unit 20A notifies the grid controlling unit 11A of the judgment result indicating that the grid control should be exercised. In that situation, the grid controlling unit 11A applies a voltage to the grid 34, at the time when the pulse descends after the X-ray pulse is radiated on the basis of the corresponding radiation conditions.

On the contrary, if the X-ray tube voltage [kV] is higher than the first threshold value (step S102: No) or if the X-ray tube current [mA] is higher than the second threshold value (step S103: No), the judging unit 20A determines that the grid control is not turned on, i.e., the grid control shall not be exercised for the determined radiation conditions (step S105). After that, the judging unit 20A notifies the grid controlling unit 11A of the judgment result indicating that the grid control shall not be exercised. In that situation, even if an X-ray pulse is radiated on the basis of the corresponding radiation conditions, the grid controlling unit 11A does not apply a voltage to the grid 34.

The configuration illustrated in FIG. 4 is merely an example. For instance, the process at step S102 where the judging process is performed by using the X-ray tube voltage [kV] and the process at step S103 where the judging process is performed by using the X-ray tube current [mA] do not necessarily have to be performed in the order stated above. For example, it is acceptable to perform the judging process using the X-ray tube voltage [kV] after performing the judging process using the X-ray tube current [mA]. Alternatively, it is also acceptable to perform only one selected from between the judging process using the X-ray tube current [mA] and the judging process using the X-ray tube voltage [kV].

Figure 5:
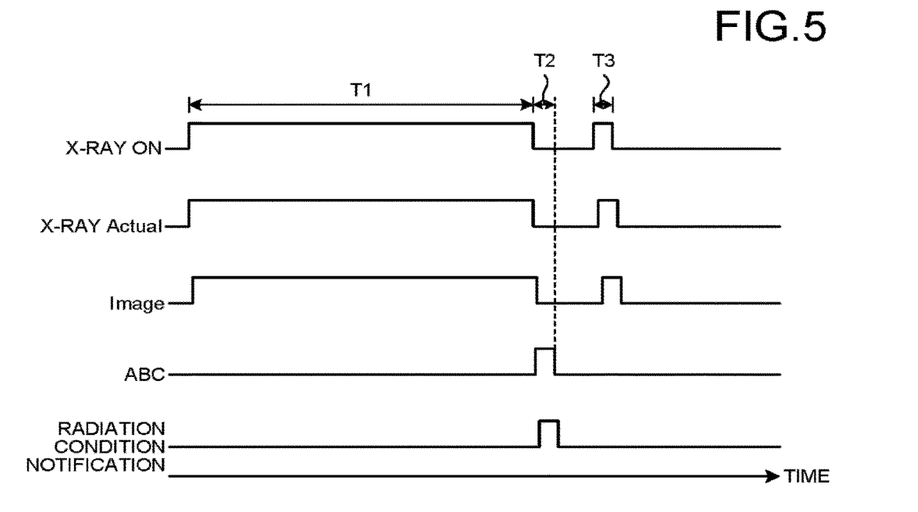
FIG. 5 is a timing chart for explaining a process performed by the X-ray diagnosis apparatus according to the first embodiment.

FIG. 5 is a timing chart for explaining a process performed by the X-ray diagnosis apparatus 100 according to the first embodiment. In FIG. 5, the horizontal direction corresponds to time (elapsed time). Further, "X-RAY ON" indicates timing with which it is possible to radiate an X-ray pulse. Further, "X-RAY Actual" indicates timing with which an X-ray pulse is actually radiated. Further, "Image" indicates timing with which an imaging process using X-rays is performed. Further, "ABC" indicates timing with which X-ray radiation conditions are determined through the ABC process performed by the determining unit 24B. Further, "RADIATION CONDITION NOTIFICATION" indicates timing with which the determining unit 24B notifies the judging unit 20A of the X-ray radiation conditions.

As illustrated in FIG. 5, during the time period T1, an X-ray pulse is radiated onto the patient P under the control of the X-ray controller 20, so that an image processing is performed by performing a continuous fluoroscopy process. After that, on the basis of the data from the imaging process, the determining unit 24B determines the X-ray radiation conditions by performing the ABC process during the time period T2 and notifies the X-ray controller 20 of the determined radiation conditions. On the basis of the radiation conditions determined by the determining unit 24B, the X-ray controller 20 performs an image taking process during the time period T3. In this situation, in accordance with the radiation conditions provided in the notification, the judging unit 20A included in the X-ray controller 20 judges whether a voltage should be applied to the grid 34 or not. After that, the judging unit 20A notifies the grid controlling unit 11A included in the high-voltage generator 11 of the judgment result. If the judgment result provided in the notification indicates that the grid control should be exercised, the grid controlling unit 11A applies a voltage to the grid 34 at the time when the pulse applied during the time period T3 descends. With this arrangement, the grid controlling unit 11A inhibits the occurrence of the wave tails 30 caused by the radiation of the pulse.

The configuration illustrated in FIG. 5 is merely an example. For instance, although FIG. 5 illustrates the example in which the continuous fluoroscopy process is performed as the fluoroscopy process, possible embodiments are not limited to this example. For instance, the present disclosure is also applicable to situations where a pulse fluoroscopy process is performed. Further, for example, it is also acceptable to apply an Automatic Exposure Control (AEC) by which an image taking time period is controlled by measuring the radiation amount during the image taking process, to the image taking process performed during the time period T3.

As explained above, the X-ray diagnosis apparatus 100 according to the first embodiment exercises the grid control in accordance with the X-ray radiation conditions. Consequently, the X-ray diagnosis apparatus 100 is able to appropriately reduce unnecessary radiation exposure caused by the wave tails.

For example, the X-ray diagnosis apparatus 100 may first perform a fluoroscopy process on a patient P and subsequently perform an image taking process by automatically determining X-ray radiation conditions on the basis of a result of the fluoroscopy process. In that situation, the X-ray diagnosis apparatus 100 automatically judges whether the grid control is necessary or not in accordance with the determined radiation conditions and exercise the grid control as appropriate. Even when the radiation conditions are automatically determined in this manner, the X-ray diagnosis apparatus 100 is able to appropriately reduce unnecessary radiation exposure caused by wave tails.

In the first embodiment, the example is explained in which the radiation conditions of the image taking process are determined on the basis of the fluoroscopy process; however possible embodiments are not limited to this example. For instance, the present embodiment may be applied to a situation where a low-dose image taking process is first performed for a preparation purpose and an image taking process is subsequently performed or to a situation where radiation conditions for an image taking process performed for the second time are determined by using radiation conditions for an image taking process performed for the first time.

Further, for example, in the first embodiment, the example is explained in which the X-ray radiation conditions are determined by the determining unit 24B; however, possible embodiments are not limited to this example. For instance, X-ray radiation conditions may be registered in advance according to an instruction from the operator. In that situation, for example, the judging unit 20A reads the radiation conditions that have already been registered and judges whether a voltage should be applied to the grid 34 of the X-ray tube 12 or not, in accordance with the read radiation conditions. After that, if the judging unit 20A has determined that a voltage should be applied, the grid controlling unit 11A applies a voltage to the grid 34. In other words, the X-ray diagnosis apparatus 100 does not necessarily have to include the determining unit 24B.

Second Embodiment

In the first embodiment, the example is explained in which the radiation conditions for the image taking process are determined on the basis of the fluoroscopy process; however, possible embodiments are not limited to this example. For instance, the present disclosure may be applied to a continuous image taking process. In the second embodiment, an example will be explained in which the present disclosure is applied to a continuous image taking process.

A configuration of the X-ray diagnosis apparatus 100 according to the second embodiment is basically the same as the configuration of the X-ray diagnosis apparatus 100 illustrated in FIG. 1, except that a part of the process is different. Thus, in the second embodiment, differences from the first embodiment will be explained, and the explanation of the same features will be omitted.

The determining unit 24B according to the second embodiment is configured to determine X-ray radiation conditions for each of X-ray pulses radiated in a series of multiple-time radiations. Further, when X-rays are radiated on the basis of radiation conditions every time the radiation conditions are determined by the determining unit 24B, the judging unit 20A according to the second embodiment judges whether a voltage should be applied or not in accordance with the radiation conditions. Next, a process according to the second embodiment will be explained with reference to a timing chart.

Figure 6:
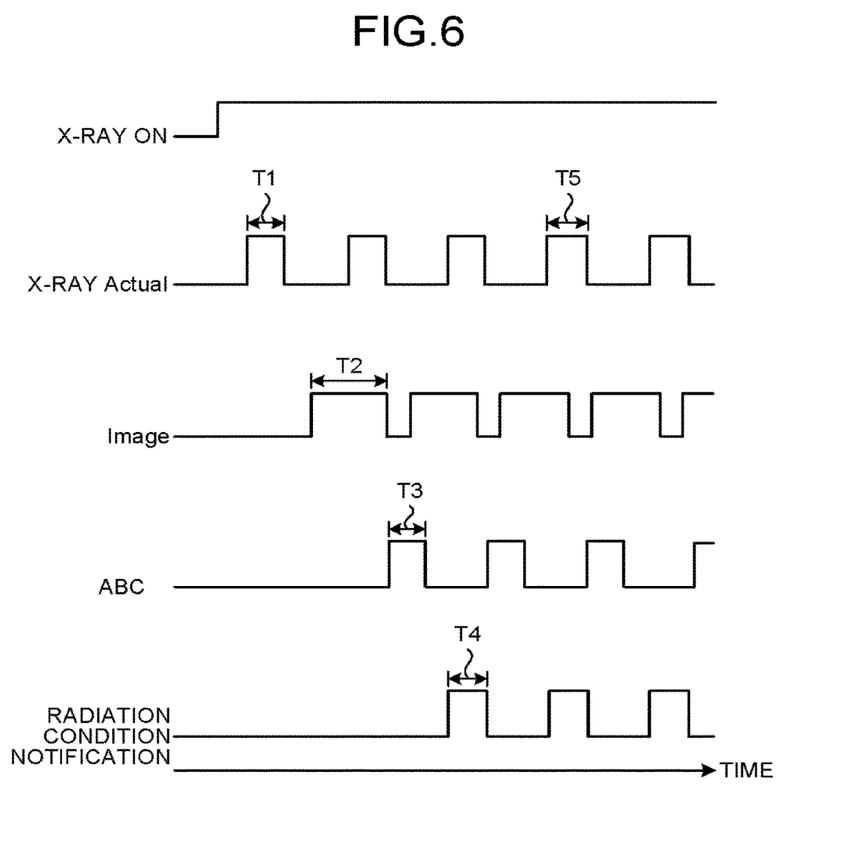
FIG. 6 is a timing chart for explaining a process performed by an X-ray diagnosis apparatus according to a second embodiment.

FIG. 6 is a timing chart for explaining a process performed by the X-ray diagnosis apparatus 100 according to the second embodiment. In FIG. 6, the horizontal direction corresponds to time (elapsed time). Further, "X-RAY ON" indicates timing with which it is possible to radiate an X-ray pulse. Further, "X-RAY Actual" indicates timing with which X-ray pulses are actually radiated. Further, "Image" indicates timing with which an imaging process using X-rays is performed. Further, "ABC" indicates timing with which X-ray radiation conditions are determined through an ABC process performed by the determining unit 24B. Further, "RADIATION CONDITION NOTIFICATION" indicates timing with which the determining unit 24B notifies the judging unit 20A of the X-ray radiation conditions.

As illustrated in FIG. 6, after an X-ray pulse is radiated onto the patient P under the control of the X-ray controller 20 during the time period T1, an image processing is performed during the time period T2. After that, on the basis of the data from the imaging process, the determining unit 24B determines the X-ray radiation conditions by performing the ABC process during the time period T3 and notifies the X-ray controller 20 of the determined radiation conditions during the time period T4. On the basis of the radiation conditions determined by the determining unit 24B, the X-ray controller 20 performs an image taking process during the time period T5. In this situation, in accordance with the radiation conditions provided in the notification, the judging unit 20A included in the X-ray controller 20 judges whether a voltage should be applied to the grid 34 or not. After that, the judging unit 20A notifies the grid controlling unit 11A included in the high-voltage generator 11 of the judgment result. If the judgment result provided in the notification indicates that the grid control should be exercised, the grid controlling unit 11A applies a voltage to the grid 34 at the time when the pulse applied during the time period T5 descends. As a result, the grid controlling unit 11A inhibits the occurrence of the wave tails 30 caused by the radiation of the pulse.

The configuration illustrated in FIG. 6 is merely an example. For instance, although FIG. 6 illustrates the example in which the X-ray radiation conditions provided in the notification from the determining unit 24B are applied to the immediately-following image taking process (i.e., the image taking process performed during the time period T5), possible embodiments are not limited to this example. For instance, the radiation conditions provided in the notification from the determining unit 24B may be applied to any image taking process performed in or after the time period T5. It should be noted however, that, it is desirable to apply the radiation conditions provided in the notification from the determining unit 24B to an image taking process performed at as an early stage as possible.

As for the judgment of whether the grid control should be exercised for the image taking processes prior to the time period T5 such as the image taking process performed during the time period T1, it is acceptable to make a judgment by performing a fluoroscopy process in advance and using the radiation conditions determined on the basis of the fluoroscopy process, as explained in the first embodiment. Alternatively, it is also acceptable to make a judgment by using initial values of the radiation conditions that are set in advance by the operator for performing a continuous image taking process.

As explained above, the X-ray diagnosis apparatus 100 according to the second embodiment is able to appropriately reduce unnecessary radiation exposure caused by wave tails, also in the continuous image taking process. For example, during a continuous image taking process, if the patient P moves or if the radiation direction of the X-rays is changed, there is a possibility that the body thickness of the patient P may vary. In that situation, if the X-ray radiation conditions become lower, wave tails may occur. To cope with this situation, when the X-ray radiation conditions become equal to or lower than certain levels, the X-ray diagnosis apparatus 100 is able to appropriately reduce unnecessary radiation exposure caused by the wave tails, by exercising the grid control.

Third Embodiment

In the first and the second embodiments, the examples are explained in which it is judged whether it is necessary to exercise the grid control for the image taking process; however, possible embodiments are not limited to this example. For instance, the present disclosure is also applicable to a situation where it is judged whether it is necessary to exercise the grid control for a pulse fluoroscopy process. Accordingly, in a third embodiment, an example will be explained in which it is judged whether it is necessary to exercise the grid control for a pulse fluoroscopy process.

In the third embodiment, an example will be explained in which a High Level Control (HLC) fluoroscopy process is performed as an example of the pulse fluoroscopy process. Further, in the third embodiment, a mode (hereinafter, "boost mode") is used for a certain period of time during the HLC fluoroscopy process for the purpose of providing images having higher image quality than normal fluoroscopy images. Usually, wave tails occur more easily during a pulse fluoroscopy process, because pulses having a lower X-ray tube current than the X-ray tube current defined in radiation conditions for an image taking process are radiated for a long period of time. For this reason, it is a common practice to exercise the grid control during normal pulse fluoroscopy processes. In contrast, the boost mode is a fluoroscopy mode in which pulses having a higher X-ray tube current than the X-ray tube current defined in radiation conditions for a fluoroscopy process are radiated for a short period of time. Thus, for example, the boost mode is effective for sites such as the heart where images may become blurry due to movements. For this reason, in the boost mode, as long as the radiation uses an X-ray tube current equal to or higher than a certain level, it is not necessary to exercise the grid control for the purpose of inhibiting the occurrence of wave tails. Nevertheless, as explained in the first embodiment, it is desirable to keep the X-ray radiation conditions low, and the boost mode is no exception. Accordingly, in the third embodiment, an example will be explained in which, when radiation conditions are determined for each pulse while the ABC process is applied to the boost mode during a pulse fluoroscopy process, it is judged whether it is necessary to exercise the grid control for the purpose of appropriately reducing unnecessary radiation exposure caused by wave tails.

A configuration of the X-ray diagnosis apparatus 100 according to the third embodiment is basically the same as the configuration of the X-ray diagnosis apparatus 100 illustrated in FIG. 1, except that a part of the process is different. Thus, in the third embodiment, differences from the first embodiment will be explained, and the explanation of the same features will be omitted.

The system controller 21 according to the third embodiment performs a pulse fluoroscopy process in the boost mode for a predetermined period of time. The boost mode is configured into the system controller 21 in advance, while the apparatus is in such a state where the operator is able to designate a mode by using the input unit 22. The reason why the boost mode is implemented for the predetermined period of time is that the X-ray radiation conditions may deviate from the specifications of the X-ray tube 12 if the boost mode is implemented longer than the predetermined period of time. Further, the boost mode can be expressed as a mode in which X-ray pulses are generated in series for a predetermined period of time without applying any voltage to the grid 34.

For example, when the pulse fluoroscopy process is started, the system controller 21 starts the boost mode. As a result, the operator is able to view an image having high image quality realized by the boost mode, when the pulse fluoroscopy process is started. Consequently, even if the image quality becomes degraded when the boost mode is ended, the viewer is able to view images while visualizing, in his/her mind, the characteristics of the image that were rendered in the image having the high image quality.

Figure 7:
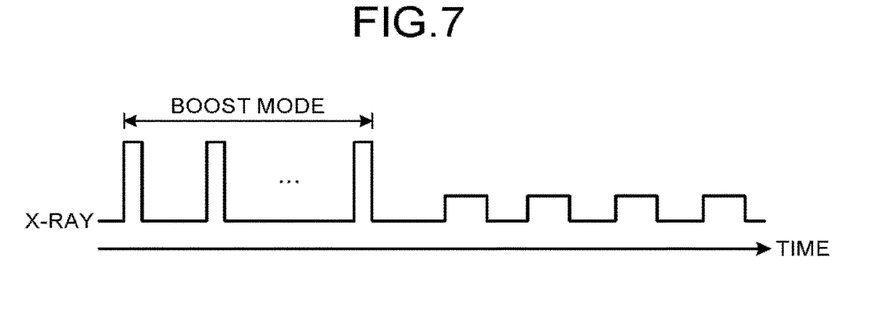
FIG. 7 is a timing chart for explaining a process performed by an X-ray diagnosis apparatus according to a third embodiment.

FIG. 7 is a timing chart for explaining a process performed by the X-ray diagnosis apparatus 100 according to the third embodiment. In FIG. 7, the vertical direction corresponds to the X-ray tube current [mA], whereas the horizontal direction corresponds to time (elapsed time). The example illustrated in FIG. 7 explains a situation where it is judged whether it is necessary to exercise the grid control in accordance with the radiation conditions during the boost mode period, whereas the normal pulse fluoroscopy process is performed outside the boost mode period.

As illustrated in FIG. 7, in the boost mode, every time an imaging process is performed by using a different one of the pulses, the determining unit 24B is configured to determine X-ray radiation conditions by performing the ABC process on the basis of the data from the imaging process. After that, the judging unit 20A judges whether a voltage should be applied to the grid 34 or not, in accordance with the determined radiation conditions. The judging unit 20A notifies the grid controlling unit 11A included in the high-voltage generator 11 of a judgment result. If the judgment result provided in the notification indicates that the grid control should be exercised, the grid controlling unit 11A applies a voltage to the grid 34 at the time when the pulse descends. With this arrangement, the grid controlling unit 11A inhibits the occurrence of wave tails caused by the pulse radiation.

Further, when the boost mode is ended after the predetermined time period has elapsed, the process proceeds to the normal pulse fluoroscopy process. During the normal pulse fluoroscopy process, the grid control is exercised every time one of the pulses is radiated. For example, when the X-ray controller 20 causes an X-ray pulse to be generated, the X-ray controller 20 notifies the grid controlling unit 11A of an instruction indicating that the grid control should be exercised. When having received the instruction provided in the notification, the grid controlling unit 11A applies a voltage to the grid 34 at the time when the pulse generated by the X-ray tube 12 descends. In this manner, the grid controlling unit 11A inhibits the occurrence of wave tails caused by the radiation of the pulse.

The example illustrated in FIG. 7 explains the situation where it is judged whether it is necessary to exercise the grid control or not, with respect to the imaging process using each of the pulses radiated during the boost mode period; however, possible embodiments are not limited to this example. It is also acceptable to judge whether it is necessary to exercise the grid control, also with respect to imaging processes using the pulses outside the boost mode period.

As explained above, the X-ray diagnosis apparatus 100 according to the third embodiment is able to appropriately reduce unnecessary radiation exposure caused by wave tails in the situation where the radiation conditions are determined for each of the pulses while the ABC process is applied to the boost mode during the pulse fluoroscopy process.

First Modification Example of Third Embodiment

In the third embodiment described above, the example is explained in which the boost mode is started at the same time when the pulse fluoroscopy process is started; however, possible embodiments are not limited to this example. For instance, it is also acceptable to start the boost mode in response to an instruction from the operator.

For example, during a pulse fluoroscopy process, the system controller 21 starts the boost mode in response to an instruction from the operator.

Figure 8:
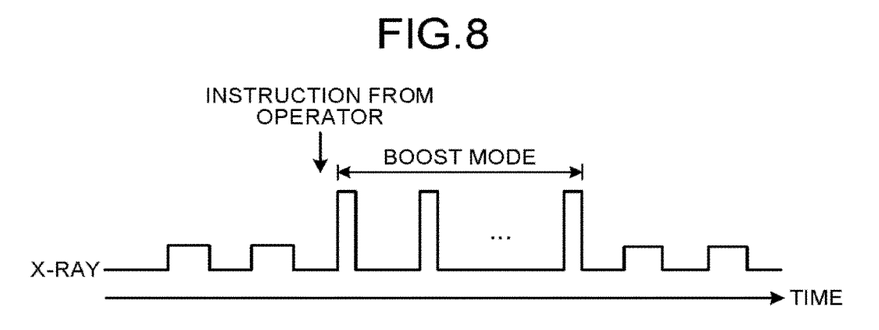
FIG. 8 is a timing chart for explaining a process performed by an X-ray diagnosis apparatus according to a first modification example of the third embodiment.

FIG. 8 is a timing chart for explaining a process performed by the X-ray diagnosis apparatus 100 according to a first modification example of the third embodiment. In FIG. 8, the vertical direction corresponding to the X-ray tube current [mA], whereas the horizontal direction corresponds to time (elapsed time).

As illustrated in FIG. 8, during a pulse fluoroscopy process, when having received an instruction indicating that the boost mode should be started, the system controller 21 starts the boost mode. With this arrangement, the operator is able to start the boost mode with arbitrary timing. In this situation, because the process of judging whether or not it is necessary to exercise the grid control in the boost mode is the same as that illustrated in FIG. 7, the explanation thereof will be omitted.

Second Modification Example of Third Embodiment

Alternatively, the boost mode described above may be started in conjunction with a predetermined instruction. The predetermined instruction may be, for example, an instruction to perform a specific image processing process such as an image processing process to realize a stent fixation display. The image processing process to realize the stent fixation display may be performed by, for example, implementing an image processing technique by which a stent marker serving as an index of a catheter position is displayed while being fixed in substantially the same position on a display screen, during an intravascular intervention treatment. When a plurality of pieces of image data are generated from a plurality of pulses in one-to-one correspondence, for example, the image processing process to realize the stent fixation display may be performed by detecting the position of the stent marker in each of the pieces of image data and correcting the pieces of image data in such a manner that the detected positions substantially match one another on the display screen. In this situation, the reason why the image processing process to realize the stent fixation display is arranged to work in conjunction with the boost mode is that it is considered desirable to display images having high image quality, because medical doctors are required to perform precise manipulations during intravascular intervention treatments.

For example, when having received a predetermined instruction that is set in advance, the system controller 21 starts the boost mode when a pulse fluoroscopy process is started.

Figure 9:
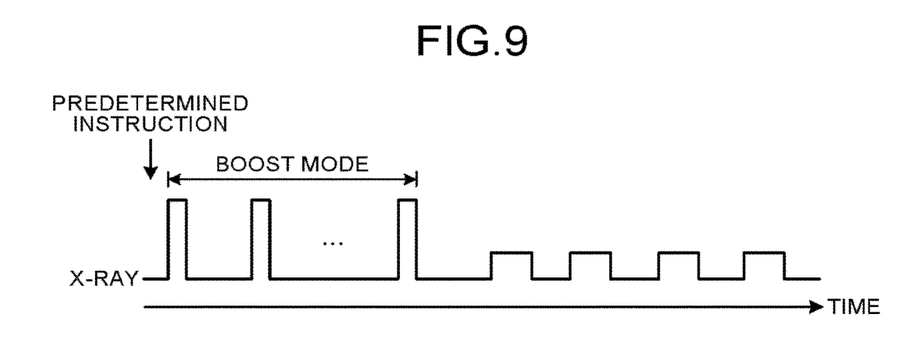
FIG. 9 is a timing chart for explaining a process performed by an X-ray diagnosis apparatus according to a second modification example of the third embodiment.

FIG. 9 is a timing chart for explaining a process performed by the X-ray diagnosis apparatus 100 according to a second modification of the third embodiment. In FIG. 9, the vertical direction corresponds to the X-ray tube current [mA], whereas the horizontal direction corresponds to time (elapsed time).

As illustrated in FIG. 9, when having received an instruction, as the predetermined instruction, from the operator indicating that an image processing process to realize a stent fixation display should be performed, the system controller 21 configures a setting so that the boost mode is started when a pulse fluoroscopy process is started. Further, when the pulse fluoroscopy process is actually started, an imaging process in the boost mode is performed at first. By using this configuration where the instruction for which it is desirable to perform an imaging process with high image quality (e.g., SMS) is arranged to work in conjunction with the boost mode, the X-ray diagnosis apparatus 100 is able to have the boost mode started automatically, upon receipt of such an instruction from the operator. In this situation, because the process of judging whether or not it is necessary to exercise the grid control in the boost mode is the same as that illustrated in FIG. 7, the explanation thereof will be omitted.

Although FIG. 9 illustrates the example in which the instruction indicating that the image processing process to realize the stent fixation display should be performed is arranged to work in conjunction with the boost mode, possible embodiments are not limited to this example. For instance, when an image processing process for which it is considered desirable to display an image with high image quality is performed in conjunction with a pulse fluoroscopy process or a continuous image taking process, it is desirable to cause the boost mode to work in conjunction therewith.

Further, the boost mode explained in the third embodiment is able to achieve the abovementioned advantageous effects even when the boost mode is implemented separately from the process of judging whether it is necessary to exercise the grid control.

Further, the constituent elements of the apparatuses illustrated in the drawings in the first to the third embodiments described above are based on functional concepts. Thus, it is not necessary to physically configure the constituent elements as indicated in the drawings. In other words, the specific modes of distribution and integration of the apparatuses are not limited to the ones illustrated in the drawings. It is acceptable to functionally or physically distribute or integrate all or a part of the apparatuses in any arbitrary units, depending on various loads and the status of use. Further, all or an arbitrary part of the processing functions implemented by the apparatuses may be realized by a Central Processing Unit (CPU) and a computer program analyzed and executed by the CPU or may be realized as hardware using wired logic. The CPU is an example of processing circuitry.

In other words, the processing functions illustrated in FIG. 1 may be realized by processing circuitry having the processing functions. For example, the grid controlling unit 11A, the judging unit 20A, the generating unit 24A, and the determining unit 24B may be realized by grid controlling circuitry serving as processing circuitry that has the functions of the grid controlling unit 11A, judging circuitry serving as processing circuitry that has the functions of the judging unit 20A, generating circuitry serving as processing circuitry that has the functions of the generating unit 24A, and determining circuitry serving as processing circuitry that has the functions of the determining unit 24B, respectively. Alternatively, for example, any of the processing functions may be realized by processing circuitry that has two or more of the processing functions illustrated in FIG. 1. For example, the generating unit 24A and the determining unit 24B may be realized by image processing circuitry serving as single processing circuitry that has the functions of the generating unit 24A and the determining unit 24B.

Further, for example, in the embodiments described above, the example is explained in which the X-ray diagnosis apparatus 100 includes the C-arm 15; however, possible embodiments are not limited to this example. For instance, the X-ray diagnosis apparatus 100 may include a supporting unit (an arm) that supports the X-ray tube 12 and the X-ray diaphragm device 13, separately from another supporting unit that supports the X-ray detector 16. In that situation, for example, the X-ray diagnosis apparatus 100 includes a mechanism for rotating and moving these supporting units.

Further, the processes explained in the embodiments and the modification examples described above may be realized by causing an image processing computer program (hereinafter, "image processing program") prepared in advance to be executed by a computer such as a personal computer or a workstation. The image processing program may be distributed via a network such as the Internet. Further, the image processing program may be recorded on a computer-recordable recording medium such as a hard disk, a flexible disk (FD), a Compact Disk Read-Only Memory (CD-ROM), a Magneto-Optical (MO) disk, a Digital Versatile Disk (DVD) and may be executed as being read from the recording medium by a computer.

According to at least one aspect of the embodiments described above, it is possible to appropriately reduce the unnecessary radiation exposure caused by the wave tails.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An X-ray diagnosis apparatus, comprising:
an X-ray tube configured to radiate X-rays, the X-ray tube including a grid;
judging circuitry configured to judge whether a voltage should be applied to the grid or not, in accordance with a radiation condition; and
grid controlling circuitry configured to, when the judging circuitry has determined that the voltage should be applied, apply the voltage to the grid,
wherein the judging circuitry determines that the voltage should be applied when an X-ray tube voltage and an X-ray tube current serving as the radiation condition are both lower than respective threshold values that are set in advance.
2. An X-ray diagnosis apparatus, comprising:
an X-ray tube configured to radiate X-rays, the X-ray tube including a grid;
an X-ray detector configured to detect the X-rays that have passed through a patient;
setting circuitry configured to set a radiation condition based on detection data of the X-rays detected by the X-ray detector,
judging circuitry configured to judge whether a voltage should be applied to the arid or not, in accordance with the radiation condition set by the setting circuitry, and
grid controlling circuitry configured to, when the judging circuitry has determined that the voltage should be applied, apply the voltage to the grid.
3. The X-ray diagnosis apparatus according to claim 2, wherein
the setting circuitry is further configured to set the radiation condition for an image taking process performed on the patient, based on the detection data of the X-rays detected by the X-ray detector during a fluoroscopy process performed on the patient, and the judging circuitry is further configured to judge whether the voltage should be applied to the grid of the X-ray tube or not during the image taking process performed on the patient, in accordance with the radiation condition set by the setting circuitry.

4. The X-ray diagnosis apparatus according to claim 2, wherein the setting circuitry is further configured to set the radiation condition for each of pulses of the X-rays radiated in a series of multiple-time radiations, and when the X-rays are radiated based on the radiation condition every time the radiation condition is set by the setting circuitry, the judging circuitry is configured to judge whether the voltage should be applied or not in accordance with the radiation condition.

5. The X-ray diagnosis apparatus according to claim 4, further comprising:

controlling circuitry configured to, during a pulse fluoroscopy process, implement a mode in which pulses of X-rays are generated in series for a predetermined time period without applying the voltage, wherein the setting circuitry is further configured to set the radiation condition for each of the pulses of the X-rays radiated in the series of multiple-time radiations in the mode.

6. The X-ray diagnosis apparatus according to claim 5, wherein the controlling circuitry is further configured to start the mode when the pulse fluoroscopy process is started.

7. The X-ray diagnosis apparatus according to claim 5, wherein, during the pulse fluoroscopy process, the controlling circuitry is further configured to start the mode in response to an instruction from an operator.

8. The X-ray diagnosis apparatus according to claim 5, wherein, when having received a predetermined instruction that is set in advance, the controlling circuitry is further configured to start the mode when the pulse fluoroscopy process is started.

* * * * *

UNITED STATES PATENT AND TRADEMARK OFFICE
CERTIFICATE OF CORRECTION

PATENT NO. : 10,159,455 B2
APPLICATION NO. : 14/872348
DATED : December 25, 2018
INVENTOR(S) : Makoto Takanaka et al.

Page 1 of 1

It is certified that error appears in the above-identified patent and that said Letters Patent is hereby corrected as shown below:

On the Title Page

Item (72) should read:
--(72) Inventors: Makoto Takanaka, Nasushiobara (JP);
               Kunio Shiraishi, Otawara (JP);
               Shinsuke Ooie, Yaita (JP);
               Kentarou Nishikawa, Nasushiobara (JP)--

Signed and Sealed this
First Day of October, 2019

Andrei Iancu
*Director of the United States Patent and Trademark Office*